(12) United States Patent
Wieland et al.

(10) Patent No.: US 8,481,802 B2
(45) Date of Patent: Jul. 9, 2013

(54) STRATIFORM PERFORATED BIOMATRICES

(75) Inventors: Martin Wieland, Coesfeld (DE); Hermann Haas, Raesfeld (DE)

(73) Assignee: MedSkin Solutions Dr. Suwelack AG, Billerbeck (DE)

( * ) Notice: Subject to any disclaimer, the term of this patent is extended or adjusted under 35 U.S.C. 154(b) by 69 days.

(21) Appl. No.: 13/154,480

(22) Filed: Jun. 7, 2011

(65) Prior Publication Data
US 2011/0305736 A1 Dec. 15, 2011

(30) Foreign Application Priority Data

Jun. 10, 2010 (EP) .................................. 10165551

(51) Int. Cl.
*A61F 15/00* (2006.01)
*A61L 15/00* (2006.01)
(52) U.S. Cl.
CPC ..................................... *A61L 15/00* (2013.01)
USPC ........................................................... 602/48
(58) Field of Classification Search
None
See application file for complete search history.

(56) References Cited

U.S. PATENT DOCUMENTS

| | | | |
|---|---|---|---|
| 3,143,208 A | 8/1964 | Sizemore, Jr. | |
| 4,789,401 A | 12/1988 | Ebinger et al. | |
| 2002/0103542 A1 | 8/2002 | Bilbo | |
| 2003/0190339 A1 | 10/2003 | Skover et al. | |
| 2004/0073151 A1 * | 4/2004 | Weston | 602/41 |
| 2011/0158963 A1 * | 6/2011 | Font Perez et al. | 424/93.7 |
| 2011/0262541 A1 * | 10/2011 | Lauritzen et al. | 424/484 |

FOREIGN PATENT DOCUMENTS

| | | |
|---|---|---|
| GB | 1102118 | 2/1968 |
| WO | 2005/060550 | 7/2005 |
| WO | WO 2010004066 A1 * | 1/2010 |

OTHER PUBLICATIONS

Zimmer® Foot and Ankle Solutions product sheet "Collagraft®" (2005) pp. 1-24 (http://www.zimmer.com/web/enUS/pdf/Zimmer_Foot_and_Ankle_System_Brochure_97-4902-101-00_2005.pdf).*
European Search Report for corresponding EP Application No. 10165551.2 mailed Nov. 15, 2010, six pages.

* cited by examiner

*Primary Examiner* — Bethany Barham
(74) *Attorney, Agent, or Firm* — Rankin, Hill & Clark LLP

(57) ABSTRACT

The present invention relates to stratiform biomatrices that are formed from regularly shaped, uniformly arranged portions which are connected to one another by continuous, straight-through perforations, and also to the use thereof as cosmetic or pharmaceutical agents, such as, in particular, as agents for wound treatment. The present invention further relates to a process for producing stratiform biomatrices of such a type, and also to the combination thereof in kit-of-parts arrangements.

20 Claims, 5 Drawing Sheets

STRATIFORM PERFORATED BIOMATRICES

The present invention relates to stratiform biomatrices that are formed from regularly shaped, evenly arranged portions which are connected to one another by continuous, straight-through perforations, and also to the use thereof as cosmetic or pharmaceutical agents, such as, in particular, as agents for wound treatment. The present invention further relates to a process for producing stratiform biomatrices of such a type, and also to the combination thereof in kit-of-parts arrangements.

Diverse agents are known in the most varied forms of administration and application for the purpose of cosmetic and therapeutic treatment of the human body. An important role is played in this connection by masks, sheets, matrices, overlays, pads, laminations or similar planar forms, since such embodiments are particularly suitable for external and planar treatment and care of the skin and also for dressing planar skin injuries or wounds. Depending on the desired aim of treatment or on the chosen field of application of the overlays, special, occasionally very specific, demands in terms of material and function are made of such compositions, in particular of their chemical composition and also their physical or biochemical mode of action and operation. Especially in the case of external dermal treatment, the complex biochemical interactions and modes of operation with the organ constituted by the skin have to be taken into consideration.

In this connection the care and protection of the skin, for example by means of a cosmetic treatment, and also the restoration, healing or alleviation of functional disorders of or injuries to the skin by means of a therapeutic treatment are of almost equal significance.

Care and prophylactic protection by means of a cosmetic treatment can be achieved, in particular, through the application and introduction of active substances, nutrients and/or grooming substances, but also by assisting or improving the physical and mechanical protective and/or barrier properties such as elasticity, smoothness, roughness, dryness or biochemical equilibrium of the skin. Here, in particular, the support, protection, regulation and also improvement of the moisture content and fat content, in particular of the so-called natural moisturizing factor (NMF) and also of the barrier function of the skin, constitutes an important element of the treatment.

In the case of an injury to or impairment of the skin, or of one of its central functions, a treatment that brings about a soothing, healing or restorative action is of particular significance. Such a therapeutic treatment can likewise be undertaken by supplying certain positively-acting active or curative substances or by means of suitable assisting physical or biochemical methods that assist and favourably influence self-healing. In this connection the type and extent of such a therapeutic treatment are dependent, in particular, on the type of the injury or functional disorder, and have to be specially matched to the affected cutaneous layers.

For both fields, the grooming cosmetic field and also the therapeutic field of skin treatment, the use of solid, dry or pre-moistened, absorbent or hydratable forms of preparation, in particular in the form of planar masks, sheets, overlays or pads, is in principle particularly suitable and also already widespread. In this connection, particularly such preparations are of interest which, in addition to the application of active substances, also already have an action in themselves that hydrates and also optionally cools the skin, or which have a positive influence on the natural wound-healing processes. This is equally relevant both for cosmetic and for therapeutic skin treatments.

In addition to these biochemical aspects, however, the geometrical and mechanical configurations of the overlays are also of great importance and have to be adapted to the respective regions of the body to be treated, in order to enable an efficient treatment of the skin.

Now the present invention relates to the special technical field of stratiform cosmetic and therapeutic overlays and implants and, in particular, specific geometrical and mechanical configurations of such stratiform overlays.

By the term 'overlay' in the sense of the present invention, a stratiform matrix is understood that is configured in the form of a sheet, fleece, pad, layer or in the manner of a mask or compress and similar and that can be applied onto at least one subregion of the human or animal body. Furthermore, by the term 'overlay', an implant for introduction into the human or animal body or into a wound is also understood, whereby implants of such a type either remain in the body and are, where appropriate, physiologically converted or degraded or can be removed within the scope of the treatment. Furthermore, by the term 'overlay' within the scope of the present invention in general also a special grooming agent or treatment agent is understood that can be moistened with hot or cold liquids which optionally contain further active substances, and can be applied onto the skin or the wound. This overlay is intended to assist and complement the general care of the skin and treatment of the wound.

Stratiform, continuous biomatrices configured in homogeneously planar manner are, for example, known in the cosmetic use as skin-treatment agents in the form of cosmetic overlays or face masks.

Also in the field of wound dressing, diverse planar configurations of wound-treatment agents on the basis of biomatrices are known. In this connection, both in the cosmetic use and in the use as wound overlay, biomatrix materials configured in planar or stratiform manner are distinguished, in particular, by a good and even, large-area applicability and by, as a rule, a good modelling capability and positionability on the skin surface to be treated.

Particularly in connection with the treatment of wounds, however, in addition an extremely high flexibility for a spatial or three-dimensional modelling capability of the stratiform materials is also desirable, in order to obtain, particularly in connection with the treatment of wounds with deep skin defects or with large wound cavities, as complete and homogeneous a packing or covering or tamponade as possible of such deeper skin defects or wound cavities.

Ordinarily for the purpose of filling deep wounds, pulverulent or gel-like wound-treatment systems have frequently found application hitherto. From the group of the powders in this connection, in particular agents such as Avitene® Flour as haemostyptic from Davol Inc. or Orahesive® from ConvaTec are known as agents for wound treatment. By way of wound-treatment agents in gel form, those on the basis of hydrogel-forming polysaccharides are ordinarily employed. Known examples here are Askina Gel® from B. Braun, Hydrosorb® Gel from Hartmann, Varihesive Hydrogel® from ConvaTech and numerous others.

Powders and gels as agents in the treatment of wounds or as haemostyptics have the disadvantage that although, on the one hand, they can be interspersed or introduced well into deep wounds or skin defects, after contact there with the liquid of the wound or with the moist surface of the area of the body being treated they can only be corrected in their positioning with difficulty or cannot be corrected at all, since for the most part they fuse with the bottom of the wound or adhere thereto. Particularly with the use of pulverulent wound-treatment agents, an even, planar application is only possible with difficulty and, as a rule, depends greatly on the skill and experience of the user.

Similar problems become evident with the use of gel-like wound-treatment agents which, although they can be modelled well to the surfaces of the wound, can only be applied homogeneously onto the surfaces of the wound to a limited extent. Furthermore, in the case of gel-like preparations, owing to the not inconsiderable water content of such preparations there is always the problem of stabilisation and preservation against microbial decay. On the one hand, this gives rise to special additional expenditure in the production of such products, and, in addition, particularly with the use of chemical preservatives, involves the risk of undesirable side-effects or incompatibility reactions in the course of use.

With the use of known and customary stratiform biomatrices in the form of planar configurations, for example in the form of sheets, fleeces, compresses, pads and similar, it is a question, as a rule, of continuous, uniform stratiform fleeces or overlays which may have been formed or tailored in the most varied geometrical shapes such as, for example, rectangles, circles and others. For example, planar or stratiform continuous wound overlays on the basis of collagen from the field of the treatment of chronic wounds or from the field of haemostyptics are known under the designation Matriderm®, Matristypt® or Puracol® from Dr. Suwelack Skin & Health Care AG or as Suprasorb® from Lohmann & Rauscher, as Promogran® from Johnson & Johnson or Systagenics or as Avitene® Sheets from Davol Inc. Moreover, known examples of planar, stratiform wound overlays on the basis of polysaccharides and others are Algisite M® from Smith & Nephew, Askina Sorb® from B. Braun and also numerous others. Planar, sheet-like wound overlays on the basis of other polysaccharides, such as, for example, Chitoskin® from Sangui BioTech GmbH or mixtures of, for example, collagen and alginate, such as, for example, Fibracol® from Johnson & Johnson, are also known and are employed as common wound-treatment agents both in the case of chronic wounds and as haemostyptics or haemostatic agents.

Such wound overlays configured in uniform or continuous homogeneously planar manner on the basis of biomatrix materials have, as a rule, only a limited flexibility and can only be fitted into wound cavities or deep wounds homogeneously and in completely packing manner to a limited extent. Consequently, deep and irregularly formed wound cavities can, for the most part, only be covered inadequately and incompletely with such biomatrix wound-treatment materials designed in uniformly planar manner and, even with the use of a very flexible fleece, as a rule a complete tamponade of the wound cannot be obtained.

Moreover, it is frequently necessary to adapt the prefabricated wound-treatment agents configured in planar manner, for example, such sheet-like layer-like or stratiform wound overlays, to irregularly shaped margins of a wound. In the case of the known materials formed in uniform, homogeneously planar manner this is done, as a rule, by tailoring prior to application. However, on the one hand this constitutes additional labour and, in addition, entails an increased risk of infection and injury, owing to handling of the wound overlays and bringing them into contact with cutting tools such as scissors, knives etc.

Overall, with stratiform wound-treatment materials configured in continuous homogeneously planar manner, such as have been known and customary hitherto, an even and homogeneous application on planar wound cavities and also a complete and homogeneous spatial covering of deep wound cavities are only insufficiently possible, and such materials are furthermore associated with the disadvantage of a further adaptation of shape by application of mechanical cutting tools.

Surprisingly, it has been found that known biomatrices configured in planar or stratiform manner, such as, for example, those on the basis of collagen but also those on the basis of natural plant hydrocolloids, can be distinctly improved in their application behaviour, modulation behaviour and absorption behaviour by being provided with continuous, straight-through perforations, these perforations being put into place in such a way that, as a result, a stratiform biomatrix is formed that is formed overall from regularly shaped, evenly arranged portions connected to one another.

A further advantage that results from this special perforation technique lies in the fact that stratiform biomatrices of such a type formed from regularly shaped, evenly arranged portions connected to one another can be brought into virtually any desired and needed size easily and quickly by simple tearing or severing along the perforations, without the additional use of cutting tools—to be rated as disadvantageous for the stated reasons—being necessary.

Planar or stratiform biomatrices that exhibit perforations are known in principle from the state of the art.

In this connection, particularly in the field of wound-treatment-agent bandaging materials, foils or biomatrices are frequently provided with a punctiform or hole-like perforation passing through the total thickness of the material, as a result of which the material is given a type of sieve structure or hole structure or pore structure. Such a perforation of the bandaging materials serves to increase or to enable the passage of gas and/or liquid through the materials. Matrices of such a type which are perforated in punctiform manner are described, for example, in DE 1 642 012, US 2002/0103542, US 2003/0190339, U.S. Pat. No. 5,060,678.

In addition, particularly in the field of wound-bandaging materials it is known and customary to form a type of perforation in the form of incisions, put into place in slit-like manner, in a matrix material, as a result of which a type of reticular structure of the matrices arises. A material that has been slit in such a manner is ordinarily also designated as meshed material. In this connection the so-called mesh process is known, in particular, from the machining of split skin which, by the placement of the regularly arranged slit-like incisions, can be drawn open to a multiple of its surface area, comparable with a traditional string bag. As a result, with comparatively small pieces of split skin it becomes possible to cover a transplantation surface that is larger by a multiple. Such a mesh-like or net-like slit-type perforation of biomatrices is known, for example, from U.S. Pat. No. 4,520,821 or from U.S. Pat. No. 6,183,496 and U.S. Pat. No. 6,261,309 or also from WO 03/035125.

In this connection, however, neither matrix materials perforated in punctiform nor slit-like manner nor meshed matrix materials form regularly shaped, evenly arranged portions connected to one another. The formation of portions of such a type connected to one another is, however, crucial for the improvement, described above, of the flexibility, in particular for a spatial modelling capability, and also for simple adaptation of the size and shape of the stratiform matrices.

Biomatrices with continuous perforations by virtue of which the formation of portions takes place are also disclosed in principle by EP 1 272 158 B1. The subject-matter of this printed patent specification is constituted by face masks consisting of a flexible carrier that is suitable for absorbing liquid, or of an absorbent carrier, which consists of at least one web-like component and which is characterised in that at least one of the components consists of at least two subcomponents which are releasably connected to one another. In the case of masks of such a type it is a question, for example, of those on the basis of collagen and also of those which are provided for use as cosmetic skin-treatment agents. The simpler application without elaborate tailoring to the body part to be treated, in particular the face, is emphasised as an advantage according to the invention. In this connection, subcomponents that have the shape of the differing face areas are formed by the perforations. The subcomponents disclosed therein are, however, not regularly shaped and evenly arranged. In addition, the subcomponents formed by the perforations disclosed therein are comparatively large, since they are provided for the purpose of covering relatively large treatment areas. As a result, however, no enhancement of the flexibility and hence of the improvement of the spatial modelling capability can be obtained such as is possible through the formation of regularly shaped, evenly arranged portions of comparatively small size, according to the present invention. Also, no indications result from the stated printed patent specification of a use of the described masks as therapeutic agent, in particular for the purpose of wound treatment or as haemostyptic. Hence the improvement of the flexibility and spatial modelling capability of stratiform biomatrices that is achieved with this special perforation technique of the present invention cannot be gathered from EP 1 272 158 B1.

From U.S. Pat. No. 3,143,208 adhesive plaster materials are known that exhibit continuous, straight-through perforations forming regularly shaped, evenly arranged portions connected to one another. By virtue of perforations placed in such a manner, the severing of portions of differing, individually desirable size is made possible. In the case of the perforated materials described therein, however, it is not a question of biomatrices and, in particular, of such materials which are applied as treatment agents onto the skin or on or in a wound or which as hydrophilic material are provided with a liquid-uptake capacity or liquid-retaining capacity in order to be suitable for classical wound treatment. Rather, synthetic covering materials in the form of self-adhesive plasters are the subject-matter of this printed patent specification. The portions formed by the perforations likewise have, in addition, a comparatively large configuration. By way of smallest subcomponents, pieces down to minimally 2×0.45 inch, corresponding to about 6.45 cm², are described. As a result, also from this printed patent specification neither do indications arise of the improvement of the flexibility and spatial modelling capability of stratiform biomatrices that is achievable with this perforation technique nor can indications be found therein of the particularly suitable use of biomatrix materials perforated in such a manner as skin-treatment agents or wound-treatment agents with high liquid-uptake capacity or liquid-retaining capacity.

Wound-treatment materials with a high flexibility and spatial modelling capability for covering wound cavities and deep skin defects are described, for example, in U.S. Pat. No. 5,928,174, U.S. Pat. No. 6,355,858 and U.S. Pat. No. 6,605,751, the improved flexibility and spatial modelling capability for the purpose of packing the wound cavities being achieved here through the placing of long incisions for the purpose of forming comb-like slits or 'free-flowing' strands of material. In this connection, such materials incised in comb-like or strand-like manner cannot be readily varied or adapted in their planar configuration. A good planar or superficial application onto a skin part to be treated and remodulation capability and uniform applicability there are also hardly possible by means of such slit materials.

A similar effect is achieved through the placing of a straight-through helical perforation for the purpose of undoing the wound-treatment material in the form of long strips or individual bands, as described in U.S. Pat. No. 5,885,237. In this connection, however, a perforation undone in the manner of a strand can also only be adapted in its planar configuration in very limited manner, as a rule at most a variation of the strand length can be effected, or a reduction of the diameter of the helically wound strands can be achieved by severing of strand parts. A variation in the geometrical surface shape is, however, likewise not readily possible here. From U.S. Pat. No. 5,885,237 it follows in addition that through the formation of such matrices formed in strand-like or band-like manner only an inadequate, incomplete tamponade of the wound is possible. For this reason, by way of biomatrix materials use is made of those which are provided with an extremely high swelling capacity, as a result of which a distinct enlargement of the volume of the matrix material occurs upon uptake of liquid, as a result of which the residual gaps can be filled out. In the case of such highly swellable matrix materials it is a question of synthetic, swellable hydrocolloids such as, for example, acrylates according to U.S. Pat. No. 5,928,174, U.S. Pat. No. 6,355,858 and U.S. Pat. No. 6,605,751, or of synthetic block copolymers as in U.S. Pat. No. 5,885,237, which can optionally be mixed with further, for example, natural polymers. A disadvantageous aspect of such matrix materials on the basis of synthetic polymers is, on the one hand, the deficient biological degradability, which particularly in the case of implant materials plays a major role, and also the, as a rule, lower biological compatibility. Furthermore, with the use of such highly swellable synthetic matrix materials the degree of swelling is not controllable or can only be controlled with difficulty. As a result, in the event of an excessive swelling in the packed wound cavity an undesirable excess of wound-treatment material and, as a result, where appropriate, an increase in the pressure in the wound cavity by reason of the excessive increase in volume may arise, having a negative effect on the treatment, since, as a result, on the one hand the healing of the wound is disturbed and, on the other hand, the patient is subjected to unnecessary wound pain.

The stratiform and optionally perforated or slit overlays known from the state of the art are consequently not provided with a sufficient flexibility for a high spatial modelling capability or modulation capability with a view to optimal covering of wound cavities and deep skin defects with simultaneous good planar applicability and modelling capability or remodulation capability with simultaneous simple and variable planar adaptation of shape and high biological compatibility and degradability, in order to be suitable both as cosmetic skin-care agent and also as therapeutic wound-treatment agent and implant.

Now the present invention sets itself the task of solving the problem of the disadvantages indicated above and, with a view to achieving this task, starts from an overlay in the form of a stratiform biomatrix (1). The stratiform biomatrix according to the invention is represented in detail in FIGS. 1 to 12, to which reference will be made in the following.

The stratiform biomatrix (1) according to the invention is characterised in that it is formed from regularly shaped, evenly arranged portions (2) which are connected to one another by continuous, straight-through perforations (3).

In this connection the term 'stratiform biomatrix' in the sense of the present invention designates an overlay formed from a substantially biocompatible carrier material, which is configured in the form of a stratum, sheet, fleece, pad, layer or in the manner of a mask or compress and similar and which has a substantially planar configuration. Such stratiform biomatrices may, in principle, also be composed of several superimposed layers in the manner of a so-called sandwich layer. In accordance with the invention the term 'a stratiform biomatrix' designates, in particular, such overlays in the aforementioned sense which have a layer thickness (shortest side length) of at most 8 mm or overall an area (area between the two longest side lengths) of at least 9 cm$^2$.

The regularly shaped, evenly arranged portions (2) of the stratiform biomatrix according to the invention connected to one another by the perforations (3) are of substantially triangular, quadrangular, honeycombed, circular or elliptical form.

In this connection, in the sense of the present invention a circular or elliptical configuration also encompasses, in principle, oval geometrical shapes, and a quadrangular configuration of the portions encompasses, in principle, all known geometrical quadrangular shapes. In particular, quadrangles with opposing parallel and equally long sides, such as parallelograms, in particular equiangular parallelograms such as rectangles or squares, as well as diamonds or rhombi or trapezoids, are encompassed by this term. From the group of the quadrangularly formed portions (2), those in the form of rectangles, squares, rhombi or parallelograms are preferred, with rectangles and squares being particularly preferred.

Furthermore, by appropriate configuration of the perforations, however, portions in any other conceivable geometrical shape or also in imaginative shapes can also be formed. For instance, it is likewise conceivable to configure the portions (2) in visually or aesthetically appealing shapes such as, for example, in heart-shaped or star-shaped manner etc.

In a preferred embodiment, however, the portions (2) are formed in conventional geometrical shapes, with a substantially quadrangular shape being particularly preferred.

In the sense of the present invention, by the term 'regularly shaped portions' it is understood that several of the portions (2) with substantially the same geometrical configuration or shape which are connected to one another by the perforations form at least one contiguous area, formed by these evenly designed portions, of the biomatrix (1), accordingly that all the portions of such an area have, for example, a rectangular or round shape etc.

Preferably all of the portions of the stratiform biomatrix (1) which are connected to one another by the perforations have substantially the same geometrical configuration or shape, as represented in exemplary manner in FIGS. 1 to 8, so in such embodiments virtually only one of the areas described above is present. By means of appropriately placed perforations in a biomatrix (1), however, it is also possible to form differing areas (6a and 6b) which, as a rule, are again evenly arranged in the stratiform biomatrix (1) with, in each instance, even regularly shaped portions in the aforementioned sense, as a result of which stratiform biomatrices (1) arise wherein, overall, portions of differing geometrical shapes may be formed within a sheet. A corresponding embodiment is represented in exemplary manner in FIG. 9 or 10.

In clarification let it be noted that the term, used in accordance with the invention, 'regularly shaped portions' is not to be understood in connection with the size of the portions, that accordingly, in particular, the term 'regularly shaped' does not mean a uniform size of all the portions forming the stratiform biomatrix. Also, the term 'regularly shaped' in the aforementioned sense does not exclude the possibility that some of the uniformly shaped portions, in particular in the outer marginal regions, are partly trimmed by the tailoring of the overall stratiform biomatrix and consequently can no longer be completely contained in the stratiform biomatrix, as is discernible, for example, in embodiments according to FIGS. 5 to 8.

The term 'evenly arranged' in the sense of the present invention means that the regularly shaped portions (2) formed by the perforations are arranged with even, recurring spacings and in uniform, recurring orientation in the stratiform biomatrix (1) or in the area of the stratiform biomatrix (1) correspondingly formed by them.

The portions (2) forming the stratiform biomatrix (1) are connected to one another by continuous, straight-through perforations (3) or are formed out of the stratiform biomatrix by these perforations. In this connection the term 'continuous perforations' designates gap-free, uninterrupted, even perforations that run over the surface of the stratiform biomatrix in uniform shape and hence, in at least one direction, form perforations of uniform shape continuing over the surface of the stratiform biomatrix. Preferably at least two continuous, straight-through perforations run in substantially parallel arrangement relative to one another over the surface of the stratiform biomatrix. The continuous, straight-through perforations are preferably linearly formed, as a result of which substantially triangular or quadrangular portions such as parallelograms, rectangles or squares are formed, as represented, for example, by FIGS. 1 to 4 or 9 and 10. Furthermore, the continuous perforations may also have a substantially zigzag contour or even combinations of zigzag and linear types of contour, such as in the case of the formation of substantially trapezoidal or honeycombed portions, this being represented in exemplary manner by FIGS. 6 and 7. In particular, in the case of the formation of circular or elliptical portions (2) the continuous perforations (3) are formed in undulatory, curvilinear or arcuate manner, as represented, for example, in FIG. 8.

The term 'straight-through perforations' designates an even, substantially evenly configured contour of the perforation over the surface of the stratiform biomatrix from a point pertaining to the outer edge of the stratiform biomatrix to a further point, substantially opposite the aforementioned point, pertaining to the outer edge of the stratiform biomatrix. In this connection, in the sense of the present invention the continuous, straight-through perforation runs in at least one direction of the surface of the stratiform biomatrix in uninterrupted and gap-free manner from outer edge to outer edge.

Preferably a continuous, straight-through perforation of such a type on substantially quadrangularly formed stratiform biomatrices can run over the entire length, width or in the diagonal direction of the surface. The term 'length' in this connection designates the longest spacing of two points. In the case, for example, of circularly designed stratiform biomatrices the continuous, straight-through perforations preferably run parallel along the diameter.

In this connection preferably at least two even, continuous perforations (3a) arranged parallel to one another run in a direction of the surface of the stratiform biomatrix and at least two further continuous even perforations (3b) arranged parallel to one another, which may be configured identically to or differently from the perforations (3a), run in at least one further direction of the surface of the stratiform biomatrix in such a manner that the continuous perforations (3a) arranged in each instance parallel to one another intersect the continuous perforations (3b) arranged in each instance parallel to one another and as a result form the regularly shaped portions (2). If the straight-through parallel continuous perforations are placed in merely two different, intersecting directions of the surface of the stratiform biomatrix, in particular quadrangular portions (2) can be formed, as represented, for example, in FIGS. 1 to 3.

In a particularly preferred embodiment in this connection, the portions (2) of the stratiform biomatrix (1) are formed from continuous linear, straight-through perforations (3a) arranged parallel to one another and from continuous linear, straight-through perforations (3b) arranged parallel to one another and intersecting the perforations (3a). If the linear, straight-through perforations (3a) arranged parallel to one another are intersected at a right angle (90° angle) by the continuous linear, straight-through perforations (3b) arranged parallel to one another, then as a result substantially rectangular portions (2) are formed, as represented in exemplary manner in FIGS. 1 and 2. It is, however, also possible to arrange the intersecting perforations (3a) and (3b) at a larger or smaller angle, for example at an angle of 45°, relative to one another, as a result of which portions (2) in the form of parallelograms can be obtained, as represented in exemplary manner in FIG. 3.

In order to form triangular portions (2), preferably straight-through, continuous parallel perforations are arranged relative to one another in three different, in each instance intersecting, contours over the surface of the stratiform biomatrix, as represented, for example, in FIG. 4 or 9.

It is also possible to cause at least two continuous straight-through perforations arranged parallel to one another to run over the surface of the stratiform biomatrix and to put into place, arranged at a right angle to these parallel perforations, parallel, evenly arranged interrupted perforations in such a manner that rectangular portions which are offset relative to one another are formed, as a result of which a pattern arises that is comparable with a brick bond in the manner of a chimney bond or heading bond. An embodiment of such a type is represented in exemplary manner in FIG. 5.

Preferred in accordance with the invention are stratiform biomatrices wherein the intersecting perforations form regular, substantially rectangular or triangular portions (2) arranged in even rows.

In principle it is possible to form the spacings between the continuous perforations of the stratiform biomatrix which are arranged substantially parallel to one another in each instance identically or differently and as a result to control the size of the portions formed by the perforations substantially through the formation of the continuous perforations or through the spacing thereof from one another. In this connection it is, for example, possible to vary the spacings between the continuous perforations arranged parallel to one another over the width or length or even over the diagonal of the stratiform biomatrix in such a way that regularly shaped, evenly arranged portions of differing size are obtained. It is, however, also possible to configure the spacings of the continuous perforations arranged in each instance parallel to one another over the entire surface of the stratiform biomatrix identically, so that portions (2) of uniform size arise. As a result, it is possible to obtain stratiform biomatrices wherein the size of the portions (2) in each instance is the same or different.

In particular, in preferred embodiments as represented above, wherein the portions (2) are formed from continuous linear, straight-through perforations (3a) arranged parallel to one another and from continuous linear, straight-through perforations (3b) arranged parallel to one another and intersecting the perforations (3a), it is possible to configure the spacings between the perforations (3a) arranged in parallel and/or between the perforations (3b) arranged in parallel and intersecting the perforations (3a) in each instance identically or differently. As a result, stratiform biomatrices can be formed that have a pattern over the surface varying in the size of the portions, as represented in exemplary manner in FIG. 2.

By such a variation of the portion size within a stratiform biomatrix it becomes possible to vary the properties thereof as regards stability and flexibility by suitable selection and combination of the portion sizes within a stratiform biomatrix, and to control them optimally in coordination with the desired use.

For instance, it is possible to configure the portions in the outer region of the stratiform biomatrix to be larger than the interior portions, as represented, for example, in FIG. 2. As a result, a selective control of the flexibility properties and modulation properties of the stratiform matrices can be obtained. Accordingly, larger portions give rise to a higher mechanical stability and improved tear strength of the stratiform biomatrices in the course of handling and application, whereas especially small portions improve the flexibility and, associated therewith, the spatial modulation capability. By combination of larger, mechanically more stable portions in the outer region of the matrices and of smaller, more flexible portions in the interior region, the features constituted by stability and flexibility can be combined in a stratiform biomatrix, and materials with high flexibility and nevertheless good ease of handling can be obtained.

The regularly shaped portions of the biomatrices according to the invention have a size of at most 5 $cm^2$, preferably of at most 4 $cm^2$, particularly preferably at most 3 $cm^2$. The regularly shaped portions preferably have a size of about 0.75 $cm^2$, preferably of about 0.5 $cm^2$, more preferably of about 0.25 $cm^2$. It is, however, also possible to form yet smaller portions having a size <0.1 $cm^2$. Particularly small portions are desirable, in particular, for the purpose of achieving a particularly high flexibility. Larger portions are preferred if a higher mechanical stability is desired. In embodiments with particularly small-part portions in the interior region of the stratiform biomatrices and with larger portions in the marginal region, interior portions having a size up to about 0.5 $cm^2$ are preferably combined with marginally arranged portions having a size $\geq 1$ $cm^2$.

The perforations (3) connecting the portions (2) to one another constitute perforations in the conventional sense and may, in principle, be formed in the stratiform biomatrix by conventional perforation processes. The perforations are preferably formed by cutting or punching within the biomatrix. Cutting may, for example, be effected by suitable knives or cutting tools such as, for example, roller-type punches or also by means of laser cutting. In this connection, in principle care is to be taken to ensure that the incision does not lead to a complete separation of the portions but is guided in such a way that enough matrix material, for example in the form of fibres or webs of material, remains between the portions, in order to connect the portions to one another.

Correspondingly, by virtue of the perforations according to the invention a type of weakening-line or nominal breaking-point is formed between the portions connected to one another by these perforations. In particular, the term 'perforations' consequently also encompasses, in the sense of the present invention, fibres or webs of material or, so to speak, thinned-out or weakened regions of biomatrix material which are formed at the outer edges of the biomatrix portions, by virtue of which the portions are connected to one another in such a manner that the totality thereof gives rise to the shape of the stratiform biomatrix formed from the assembled portions.

In addition to the production of perforations by simple incising of the biomatrices, in particular also perforations with a selective width are preferred. The gap width between the portions (2) may in this connection range from a simple incision (virtually without spacing) to the six-fold, preferentially four-fold, particularly preferably two-fold, layer thickness of the stratiform biomatrix. In the case of a gap width corresponding to at least the two-fold layer thickness of the biomatrix or of the portions, a capability for torsion or twisting of the individual elements relative to one another by 180° is made possible, without the portions themselves having to be bent or folded or the perforations that connect the portions being undone. As a result, the flexibility and adaptation of the appropriately perforated biomatrix to irregular surface structures and in particular to cavities such as wound cavities can be further improved. A schematic representation of a perforation widened in such a manner or of a gap of such a type between the portions (2) forming the stratiform biomatrix is shown by FIG. 11. FIG. 12a shows a schematic side view of two portions (2) connected to one another, which are connected to one another centrally. If the gap width formed between the portions (2) corresponds to the layer thickness of the biomatrix and hence to the layer thickness of the portions (2), the portions can be rotated by 180° and positioned virtually on top of one another without the perforation being undone, as represented schematically in FIG. 12b. FIG. 12c shows a schematic side view of two portions (2) connected to one another, which are connected to one another at the edge. If the gap width formed between the portions (2) corresponds to the two-fold layer thickness of the biomatrix and hence to the two-fold layer thickness of the portions (2), the portions can be rotated by 180° and positioned virtually on top of one another without the perforation being undone, as represented schematically in FIG. 12d.

In accordance with the invention the stratiform biomatrix and hence also the portions forming the stratiform biomatrix have a thickness (defined as the shortest spacing of two points, i.e. layer thickness) of at most 8 mm. The stratiform biomatrix preferably has a layer thickness of up to 5 mm, more preferably up to 3 mm.

A correspondingly large spacing between the individual portions (2) further enables an easier handling in the course of the severing of smaller segments or even of individual portions (2). By virtue of a wider perforation gap, more space arises for grasping the units or segments to be separated out or for applying the chosen cutting tools.

By virtue of the perforations (3) by which the portions (2) are connected to one another it is possible to sever or to separate smaller segments of variable size out of the stratiform biomatrix along the perforations. In this connection the size of such smaller segments that are capable of being separated out is determined substantially by the chosen perforation. By way of smallest subunit that is capable of being separated out, an individual one of the portions (2) can be obtained. A stratiform biomatrix reduced by an individual portion (2) can accordingly be regarded as the largest subunit that is capable of being separated out or severed. As a matter of principle, undoing along each of the formed perforations (3) is possible, by which, in principle, a separating-out of subsegments with high individual planar configuration is possible. For example, it is possible to sever smaller parts of variable shape from the stratiform biomatrix (1) and to use them separately by way of smaller, individually shaped overlay. This is particularly advantageous for the purpose of adapting the stratiform biomatrices to irregularly formed, planar treatment areas or wound margins. In addition, it is conceivable to separate out of the stratiform biomatrix (1) at least one interior subsegment, in order, as a result, to form one or more openings of variable shape and size and also optionally of variable arrangement in the stratiform biomatrix (1) and to use the stratiform biomatrix (1) which has been provided with the one or more variable openings or recesses in such a manner by way of overlay in the sense of the invention.

In principle, the severing of subsegments from the stratiform biomatrix (1) in the sense of the present invention also encompasses the undoing of one or more perforations, whereby the subsegments or portions still remain connected to the stratiform biomatrix (1) by means of a further perforation, so that by virtue of the undone perforation no complete release or severing of the subsegments or portions (2) from the biomatrix takes place, but rather a type of incision or slitting of the stratiform biomatrix (1) takes place. Incisions or slits of such a type can, in turn, be varied in their length, size or configuration (e.g. linear, cross-shaped, star-shaped etc.).

Hence the present invention also relates, in particular, to a stratiform biomatrix (1) that is formed from regularly shaped, evenly arranged portions (2) which are connected to one another by continuous, straight-through perforations (3) and that by severing of one of more subsegments of variable size and shape, which are formed from at least one of the regularly shaped portions (2), is capable of being varied along the perforations (3) as regards its size, shape and/or configuration.

The cutting-through or undoing of the perforations (3) and hence the adaptation of the configuration of the biomatrix (1), such as, in particular, the disassembling of the stratiform biomatrix (1) according to the invention into smaller subsegments or even into the individual portions (2), may, for example, be effected by simple tearing, for example manually, along the chosen perforation contour, thus forming the desired shape of the subsegment to be separated out. Alternatively, smaller segments or the portions (2) may also be severed with the assistance of suitable aids such as scissors or a knife. By reason of the nominal breaking-points formed by the perforations, in this connection use may advantageously also be made of cutting tools that are not very sharp and hence comparatively harmless.

In principle, the subsegments formed from the biomatrix (1) by severing may be used simultaneously or alternatively also separately, for example at a later time.

FIGS. 1 to 12 elucidate the subject-matter of the present invention in exemplary manner and represent various possible configurations and embodiments of the stratiform biomatrix according to the invention. The reference symbols used therein refer to the above explanatory remarks:

Figure 1:
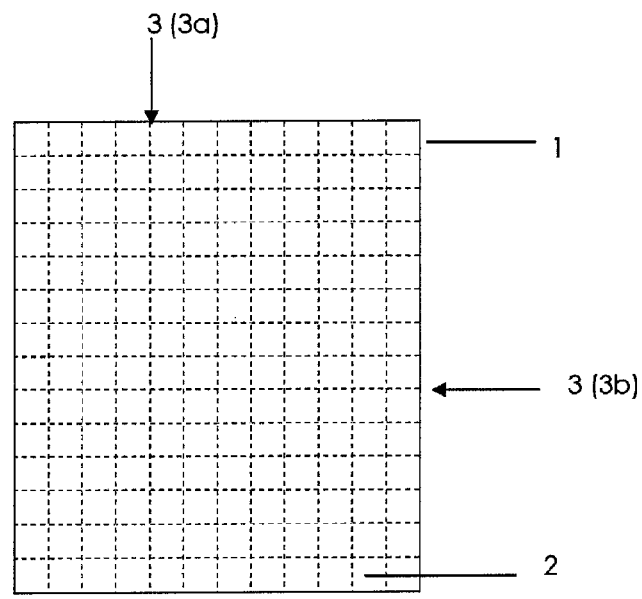
FIG. 1 shows an exemplary embodiment of the stratiform biomatrix according to the invention, wherein the portions connected by the continuous, straight-through perforations have square form.
Figure 2:
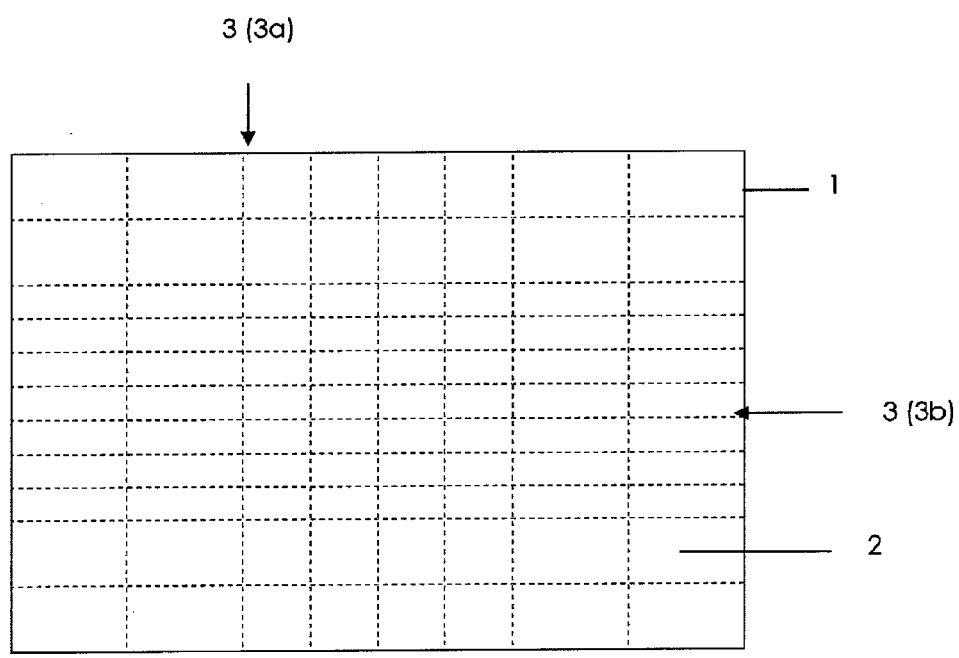
FIG. 2 shows an exemplary embodiment of the stratiform biomatrix according to the invention, wherein the spacings between the continuous, straight-through perforations arranged in parallel are variable, as a result of which portions of varying size are formed.
Figure 3:
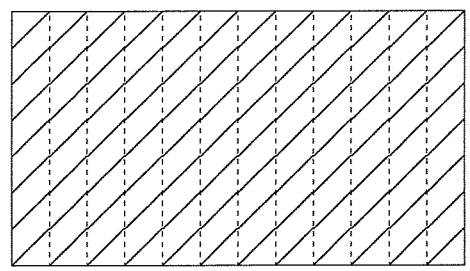
FIG. 3 shows an exemplary embodiment of the stratiform biomatrix according to the invention, wherein the portions connected by the continuous, straight-through perforations are formed as parallelograms.
Figure 4:
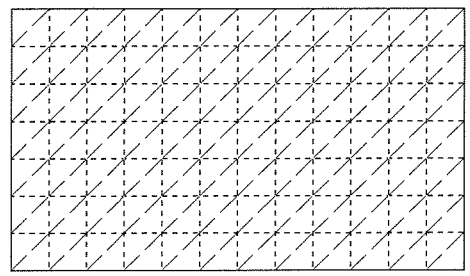
FIG. 4 shows an exemplary embodiment of the stratiform biomatrix according to the invention, wherein the portions connected by the continuous, straight-through perforations are formed as triangles.
Figure 5:
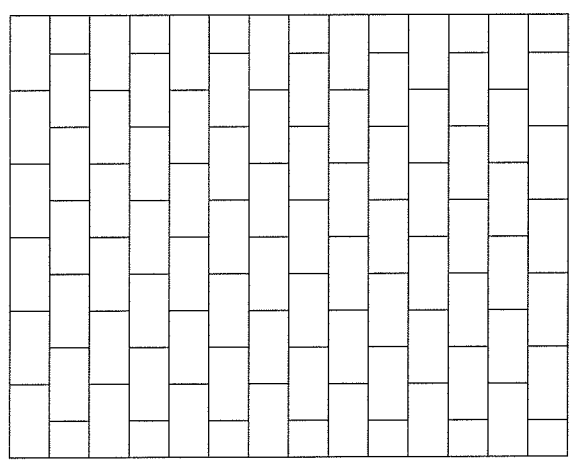
FIG. 5 shows an exemplary embodiment of the stratiform biomatrix according to the invention, wherein the perforations are formed in such a manner that rectangular portions which are offset relative to one another are formed, as a result of which a pattern arises that is comparable with a brick bond in the manner of a chimney bond or heading bond.
Figure 6:
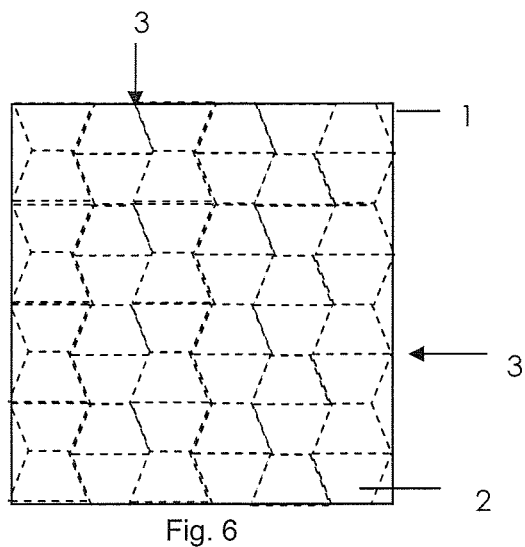
FIG. 6 shows an exemplary embodiment of the stratiform biomatrix according to the invention, wherein the portions connected by the continuous, straight-through perforations have trapezoidal form.
Figure 7:
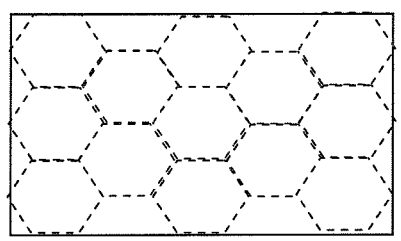
FIG. 7 shows an exemplary embodiment of the stratiform biomatrix according to the invention, wherein the portions connected by the continuous, straight-through perforations have honeycombed form.
Figure 8:
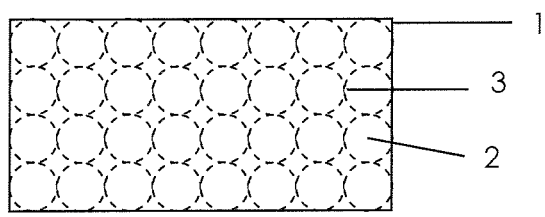
FIG. 8 shows an exemplary embodiment of the stratiform biomatrix according to the invention, wherein the portions connected by the continuous, straight-through perforations have circular form.
Figure 9:
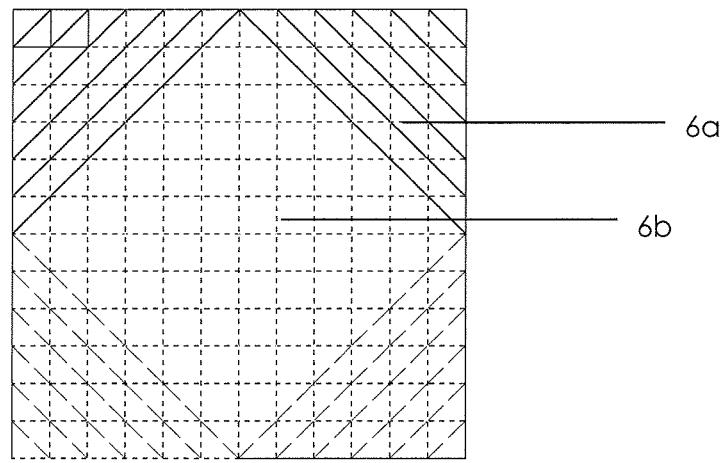
FIG. 9 shows an exemplary embodiment of the stratiform biomatrix according to the invention, wherein the portions connected by the continuous, straight-through perforations are formed in differing geometrical shapes, so that evenly arranged areas (6a) with portions formed as triangles and a further area (6b) with portions formed as squares are formed.
Figure 10:
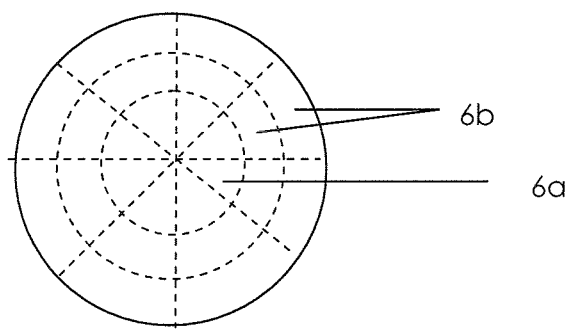

FIG. 10 shows an exemplary embodiment of the stratiform biomatrix according to the invention, wherein the portions connected by the continuous, straight-through perforations are formed in differing geometrical shapes by further circular perforations of smaller radii and also straight-through perforations intersecting at the midpoint being put into place on a biomatrix which is circular overall, as a result of which areas (6a, 6b) with portions shaped substantially in the manner of a slice of cake and with arcuate portions are formed.

Figure 11:
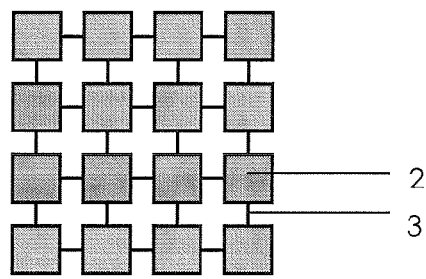

FIG. 11 shows a schematic representation of a widened perforation or of a perforation (3) formed as a gap between the portions (2) forming the stratiform biomatrix.

Figure 12A:
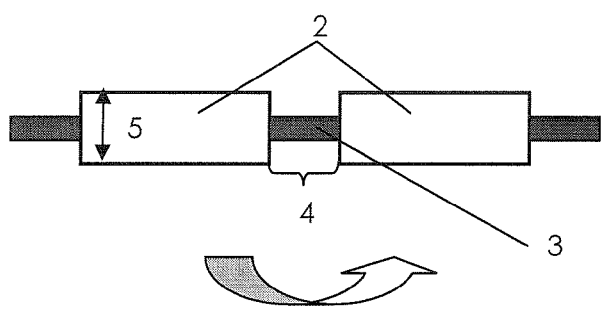

FIG. 12a shows a schematic side view of two portions (2) connected to one another, which are connected to one another centrally by a perforation (3) and wherein the perforation forms a gap (4) between the portions (2), and wherein the gap (4) has a width corresponding to the layer thickness (5) of the biomatrix and hence to the layer thickness (5) of the portions (2).

Figure 12B:
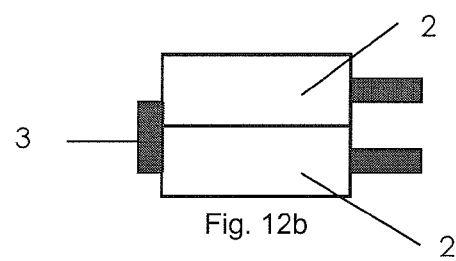

FIG. 12b shows a schematic side view wherein two of the portions (2) connected to one another by a perforation (3) have been rotated by 180° relative to one another without the perforation (3) being undone.

Figure 12C:
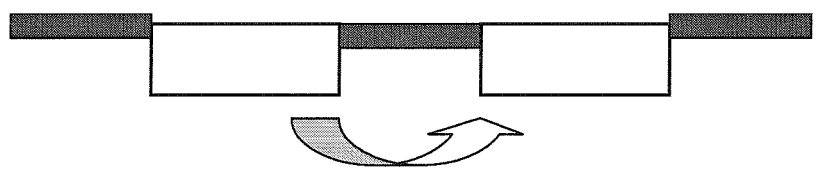

FIG. 12c shows a representation corresponding to FIG. 12a, wherein the portions (2) are connected to one another at their edges by the perforation (3).

Figure 12D:
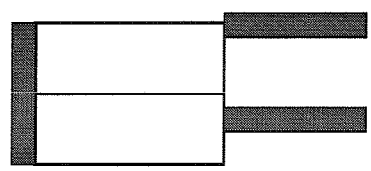

FIG. 12d shows a representation corresponding to FIG. 12b, wherein the portions (2) are connected to one another at their edges by the perforation (3).

In FIGS. 1 to 12 the reference symbols have the following significance:
1 stratiform biomatrix
2 portion
3 perforation
3a, 3b intersecting perforations
4 perforation formed as a gap
5 thickness of the stratiform biomatrix or of the portions
6a, 6b differing areas of the stratiform biomatrix with, in each instance, regularly shaped portions In the following the structural composition of the stratiform biomatrix according to the invention will be described in more detail.

In accordance with the invention the stratiform biomatrix includes a carrier material that is suitable for the use according to the invention as skin overlay or wound overlay, optionally also for the application of active substances and grooming substances, for the uptake of liquids.

In this connection the stratiform biomatrix may either be formed completely from the carrier material or may consist thereof to a predominant extent. For example, the stratiform biomatrix may be based on a carrier material to which additional active substances and/or auxiliary substances have been added, or the stratiform biomatrix based on a carrier material may, in addition, exhibit an additional coating.

The use of the stratiform biomatrices according to the invention preferably takes place in dry form. However, a use in moistened or pre-moistened form is also possible, as well as a use in which a moistening is undertaken in the course of the use or treatment.

Furthermore, the carrier material has to be selected in such a way that said material has a sufficient stability in order to be able to be converted, by tailoring and perforating, into the stratiform biomatrices according to the invention. Furthermore, the stratiform biomatrices according to the invention have to have a sufficient mechanical stability in order to remain dimensionally stable and in particular not to tear also during use or in the course of application, in particular in the course of the separating of perforated segments and also in the course of the applying and modelling of the stratiform biomatrix or of individually severed segments thereof onto the body region to be treated, in each instance both in the dry state and in the moistened state.

The carrier material is preferentially chosen from the group of the natural hydrophilic materials, i.e. materials that are capable of being wetted with water. It is preferably a so-called structure-former or a structure-forming hydrocolloid, accordingly a partly water-soluble or water-swellable natural, structure-forming polymer. Particularly preferred are structure-forming hydrocolloids from the group of the proteins, of the polysaccharides and/or of the glucosaminoglycanes.

Particularly preferably the carrier material of the stratiform biomatrix is selected from the group of the proteins, such as, for example, collagen, for example soluble or insoluble, fibrillar, animal or plant collagen, or gelatine, elastin, keratin, fibroin, albumins, globulins such as lactoglobulin, milk proteins such as casein. In this connection collagen is quite particularly preferred, optionally also in a mixture with further fibrillar proteins or in a mixture with gelatine or particularly preferably in a mixture with elastin. In the case of carrier materials on the basis of collagen it is preferably a question of those which are regenerated and produced by processes known from the state of the art and, for example, from DE 40 28 622 or from DE 103 50 654. The collagen carrier materials that are preferred in accordance with the invention are distinguished, in particular, by outstanding hydration properties and by a good liquid-uptake capacity or absorbency, an aspect which is advantageous in particular with a view to taking up large amounts of liquid, for example in the case of heavily bleeding wounds or in the case of wounds with a high degree of secreted wound liquid, and also by the anti-irritant and skin-soothing properties thereof, this being advantageous in the use according to the invention in skin treatment. By reason of the structural similarity to human skin and human tissue, types of collagen are preferably selected that occur in skin and tissue, in particular collagen of types I, III and V. As a result, the particularly good compatibility and biocompatibility of such collagen carrier materials according to the invention is determined. The agents obtainable by this means are furthermore biologically degradable in the body and can, when they remain in a wound, for example in the case of use as implant, be metabolised in natural manner. As a result, carrier materials of such a type are particularly suitable for the production of wound-treatment agents or haemostyptics for use as implant. The collagen carrier material that is used in accordance with the invention is preferably obtained from sources of collagen of bovine, equine and porcine origin. Bovine collagen is quite particularly preferred. The collagen can be obtained from the conventional sources such as hides or sinews by conventional processes.

Furthermore, use may also be made of collagen materials that have been subjected to a crosslinking reaction. In this case a thermal crosslinking, so-called dehydrothermal crosslinking, is preferred. Furthermore, crosslinking with chemical crosslinkers is possible. These include, in particular, aldehydes such as glutaraldehyde; carbodiimides such as EDC; isocyanates; epoxides or imidazoles, with the epoxide from the group of the chemical crosslinkers being particularly preferred.

Likewise preferred carrier materials that are selected from the group of the polysaccharides include, for example, homoglycanes or heteroglycanes, such as, for example, alginates, especially sodium alginate or calcium alginate or mixtures thereof, carrageen, pectins, tragacanth, guar gum, carob-bean flour, agar-agar, gum arabic, xanthan, natural and modified starches, dextranes, dextrin, maltodextrins, chitosan, glucanes such as β-1,3-glucane or β-1,4-glucane, cellulose etc. Particularly preferred polysaccharides are alginates, in particular sodium alginates and calcium alginates or mixtures thereof.

The group of the carrier materials that are selected from the group of the polysaccharides likewise includes such materials that have been subjected to a crosslinking. In particular, crosslinked polysaccharides include alginates crosslinked with calcium ions.

Glucosaminoglycanes (mucopolysaccharides) include, for example, hyaluronic acid, chondroitin sulfate, dermatan sulfate, keratan sulfate, heparan sulfate, heparin etc. Hyaluronic acid is particularly preferred.

Furthermore, use may also be made of carrier materials that have been selected from the group of the bioabsorbable synthetic or modified natural polymers, including, for example, polylactides or polylactic acids (PLA), polyglycolic acid (PGA), polycaprolactones (PCL), polydioxanones (PDO), polylactide coglycolides (PLGA), polytrimethylene carbonate etc.

Use may also be made of mixtures of at least two different carrier materials from the aforementioned carrier materials. In this connection, in particular mixtures, for example of collagen and gelatine or of collagen and alginates or of alginates and hyaluronic acid, optionally also in a mixture with further of the stated carrier materials, and also mixtures of the aforementioned bioabsorbable synthetic or modified natural polymers with collagen or alginate, are preferred.

As a matter of principle, the carrier materials of the stratiform biomatrix according to the invention may also contain small amounts of synthetic and/or semi-synthetic and/or modified natural polymers, such as, for example, those which have been selected from the group comprising, for example, cellulose ethers, polyvinyl alcohol, polyvinyl pyrrolidone, synthetic cellulose derivatives such as methylcellulose, carboxycellulose, carboxymethylcellulose such as, for example, sodium carboxymethylcellulose, cellulose esters, cellulose ethers such as hydroxypropylcellulose, cationised celluloses or cationised starches etc., polyacrylic acid, polymethacrylic acid, poly(methylmethacrylate) (PMMA), polymethacrylate (PMA), polyethylene glycols, polyurethanes, polyurea compounds etc. and mixtures thereof. A preferred synthetic polymer is polyacrylate or polyacrylic acid, which quite particularly preferably, for example, may be contained in the stratiform biomatrices in a mixture with carrier materials that have been selected from the alginates. Preferred semi-synthetic or modified natural polymers are those including cellulose, carboxymethylcellulose, cationised celluloses or cationised starches.

In this connection the proportion of such synthetic and/or semi-synthetic and/or modified natural polymers in the stratiform biomatrices according to the invention lies, as a rule, below 40 wt. %, more preferably below 30 wt. %, still more preferably below 20 wt. %, in each instance relative to the total weight of the dry stratiform biomatrix.

Quite particularly preferred, however, are those stratiform biomatrices which contain no synthetic carrier materials, in which connection the bioabsorbable synthetic or modified natural polymeric carrier materials described above are not meant here.

The proportion of the aforementioned bioabsorbable synthetic or modified natural polymers in the stratiform biomatrices according to the invention lies, as a rule, below 70 wt. %, more preferably below 60 wt. %, still more preferably below 50 wt. %, in each instance relative to the total weight of the dry stratiform biomatrix.

In accordance with the invention the use of crosslinked carrier materials for producing the stratiform biomatrix according to the invention is particularly preferred, since crosslinked materials are provided with a particularly high mechanical stability. As a result, stratiform biomatrices including crosslinked carrier materials are particularly well suited in order to place the perforations according to the invention in position. Furthermore, stratiform biomatrices according to the invention that have been mechanically stabilised in such a manner are also particularly well suited for the use and application according to the invention, since, on the one hand, they have good stability, so that in the course of separating the perforations the severing of the subsegments of the desired shape and size without damage to further parts of the stratiform biomatrix or to the parts to be separated out and, on the other hand, the application and modelling capability of the stratiform biomatrix or of the parts severed therefrom on the body region to be treated are facilitated.

Furthermore, the stratiform biomatrices may have been laminated, or the stratiform biomatrices may be constituted by carrier materials in the form of multi-layer laminations connected to one another. By way of laminates, use may be made of conventional materials known from the state of the art, such as, for example, fibres, fleeces, nets, films or foils consisting of suitable materials such as, for example, rayon, cellulose, polyethylene (PE) or polyurethane (PU) or other synthetic or semi-synthetic polymers/copolymers, which can be firmly connected in the sense of the present invention to the carrier materials by conventional methods, for example by bonding, heat laminating, crosslinking etc. A lamination of such a type is particularly suitable in order to enhance the mechanical stability of the carrier materials for the purpose of producing the stratiform biomatrices according to the invention. In this connection the lamination is preferably applied onto the carrier material prior to the placing of the perforations according to the invention.

Carrier materials that are suitable for producing the stratiform biomatrix according to the invention may be produced by customary processes, as described, for example, in DE 40 28 622, DE 103 50 654, in WO 2004/104076, in WO 2005/113656 or in WO 2008/020066 from the applicant.

The carrier materials of the stratiform biomatrix according to the invention exhibit good biocompatibility and are, in particular, skin-compatible and mucous-membrane-compatible and do not exhibit a toxicological potential either in the course of use on intact skin or in the course of introduction into one of the lower cutaneous layers, for example in wounds that exhibit an injury to, or destruction of, the natural cutaneous structure. The polymers to be used in accordance with the invention also do not bring about any irritation effects or other incompatibility reactions whatever in the course of application. They are pharmacologically totally harmless and consequently optimally suitable as polymer material for the cosmetic and pharmaceutical dermal uses according to the invention.

The stratiform biomatrix according to the invention may furthermore include at least one active substance. Active substances include, in particular, cosmetic or therapeutic or pharmaceutical active substances that are suitable for external use. Accordingly, in the case of such compositions according to the invention it is preferably a question of cosmetic or therapeutic agents.

Cosmetic agents or agents in the sense of the invention that have been produced by using cosmetic active substances are substantially agents in the sense of the *Lebensmittel-, Bedarfsgegenstände-und Futtermittelgesetzbuch* (*LFGB*) [German Food, Commodities and Feed Statute Book], i.e. substances or preparations consisting of substances that are intended to be used externally on humans for the purpose of cleaning, grooming or for influencing appearance or body odour or for conveying olfactory impressions, unless they are predominantly intended to alleviate or eliminate diseases, afflictions, bodily defects or pathological complaints. In this sense, in the case of the cosmetic articles that are used in accordance with the invention it is a question, for example, of bath preparations, skin-washing and skin-cleaning agents, skin-care agents, in particular facial-skin-care agents, eye cosmetics, lip-care agents, nail-care agents, foot-care agents, hair-care agents, in particular hair-washing agents, hair-conditioning agents, hair softeners etc., light-screening agents, skin-tanning and skin-brightening agents, depigmentation agents, deodorants, antihydrotics, hair-removing agents, insect repellents etc., or agents of such a type in combination.

Examples of cosmetically active compounds, optionally also, for example, of dermatological, therapeutically active compounds include: anti-acne agents, antimicrobial agents, antiperspirants, astringent agents, de-odorising agents, hair-removing agents, conditioning agents for the skin, skin-smoothing agents, agents for intensifying the hydration of the skin, such as, for example, glycerin or urea, sunscreen agents, keratolytics, radical-interceptors for free radicals, antiseborrhoeics, antiflaking agents, antiseptic active substances, active substances for treating the signs of skin ageing and/or agents that modulate the differentiation and/or proliferation and/or pigmentation of the skin, vitamins such as vitamin C (ascorbic acid) and their derivatives, such as, for example, glycosides such as ascorbyl glucoside, or esters of ascorbic acid, such as sodium ascorbyl phosphate or magnesium ascorbyl phosphate or ascorbyl palmitate and ascorbyl stearate, L-ascorbic acid phosphate esters, alkali-metal salts such as sodium salts and potassium salts of L-ascorbic acid phosphate esters; alkaline-earth-metal salts such as magnesium salts and calcium salts of L-ascorbic acid phosphate esters; trivalent metal salts such as aluminium salts of L-ascorbic acid phosphate esters; alkali-metal salts of L-ascorbic acid sulfate esters such as sodium salts and potassium salts of L-ascorbic acid sulfate esters; alkaline-earth-metal salts such as magnesium salts and calcium salts of L-ascorbic acid sulfate esters; trivalent metal salts such as aluminium salts of L-ascorbic acid sulfate esters; alkali-metal salts such as sodium salts and potassium salts of L-ascorbic acid esters; alkaline-earth-metal salts such as magnesium salts and calcium salts of L-ascorbic acid esters; and trivalent metal salts such as aluminium salts of L-ascorbic acid esters;

active substances with irritant side-effect, such as alpha-hydroxy acids, β-hydroxy acids, alpha-keto acids, β-keto acids, retinoids (retinol, retinal, retinoic acid), anthralins (dioxyanthranol), anthranoids, peroxides (in particular, benzoyl peroxide), minoxidil, lithium salts, antimetabolites, vitamin D and its derivatives; catechols, flavonoids, ceramides, polyunsaturated fatty acids, essential fatty acids (e.g. gamma-linolenic acid), enzymes, coenzymes, enzyme inhibitors, hydrating agents, skin-soothing agents, detergents or foam-forming agents, and inorganic or synthetic matting fillers, or decorative substances such as pigments or dyestuffs and colouring particles for foundations, make-up formulations, and other agents for cosmetic beautification and colour fashioning of eyes, lips, face etc. and also abrasive agents.

Furthermore, extracts of plant active substances and extracts or individual substances obtained therefrom may be mentioned. Generally, the extract of plant active substance is, as a rule, selected from the group consisting of solid plant extracts, liquid plant extracts, hydrophilic plant extracts, lipophilic plant extracts, individual plant components; as well as mixtures thereof, such as flavonoids and their aglycones: rutin, quercetin, diosmin, hyperoside, (neo)hesperidin, hesperitin, ginkgo biloba (e.g. ginko flavone glycosides), Crataegus extract (e.g. oligomeric procyanidins), buckwheat (e.g. rutin), *Sophora japonica* (e.g. rutin), birch leaves (e.g. quercetin glycosides, hyperoside and rutin), elder blossom (e.g. rutin), lime blossom (e.g. essential oil with quercetin and farnesol), St. John's wort oil, (e.g. olive-oil extract), calendula, arnica (e.g. oily extracts of the blossoms with essential oil, polar extracts with flavonoids), melissa (e.g. flavones, essential oil); immunostimulants: *Echinacea purpurea* (e.g. alcoholic extracts, fresh vegetable juice, pressed juice), *Eleutherokokkus senticosus*; alkaloids: caffeine, theine, theobromine, rauwolfia (e.g. prajmaline), evergreen (e.g. vincamine); further botanicals: aloe, horse chestnut (e.g. aescine), garlic (e.g. garlic oil), pineapple (e.g. bromelains), ginseng (e.g. ginsenosides), milk-thistle fruits (e.g. extract standardised to silymarin), mouse-thorn root (e.g. ruscogenine), valerian (e.g. valepotriates, valerian tincture), kava kava (e.g. kavalactones), hop flowers (e.g. hop bitters), passifloraceous extract, gentian (e.g. ethanol. extract), anthraquinone-containing drug extracts, for example, aloin-containing aloe-vera juice, pollen extract, algae extracts, liquorice-root extracts, palm extract, *Galphimia* (e.g. mother tincture), mistletoe (e.g. aqueous ethanol. extract), phytosterols (e.g. beta-sitosterol), mullen flowers (e.g. aqueous alcoholic extract), *Drosera* (e.g. liqueur-wine extract), sea-buckthorn fruits (e.g. juice obtained therefrom or sea-buckthorn oil), marshmallow root, primrose-root extract, fresh plant extracts from mallow, comfrey, ivy, horsetail, yarrow, ribwort (e.g. pressed juice), stinging nettle, celandine, parsley; plant extracts from *Norolaena lobata, Tagetes lucida, Teeoma siems, Momordica charantia*, and aloe-vera extracts.

As distinct from the active substances described above which are used substantially in beauty culture, in the case of the therapeutic active substances (medicaments) it is a question of those which in the sense of the Arzneimittelgesetz [German Drugs Act] are, inter alia, intended to heal, alleviate or prevent diseases, afflictions, bodily defects or pathological complaints. In accordance with the invention, in particular such agents or active substances are suitable which are intended for external or transdermal use, in particular in the field of wound treatment and wound healing and also in the field of the treatment of burn injuries, in particular for the initial dressing of burns.

In the case of active substances for a dermal or transdermal use it is a question, in particular, of cutaneously active but also of transdermal active substances. They include, for example: agents for treating burn injuries, agents for treating skin diseases, externally applicable analgesics, for example, dextropropoxyphene, pentazocine, pethidine, buprenorphine; anti-rheumatics/antiphlogistics (NSAR), for example, indomethacin, diclofenac, naproxen, ketoprofen, ibuprofen, flurbiprofen, salicylic acid and salicylic-acid derivatives such as acetylsalicylic acid, oxicams; steroid hormones, for example, betamethasone, dexamethasone, methyl prednisolone, ethinyl estradiol, medroergotamine, dihydroergotoxine; gout remedies, for example, benzobromarone, allopurinol; external dermatics, antihistamines, antibiotics inclusive of antibacterial agents such as, for example, colloidal silver and silver salts, antimycotics, peptide medicinal substances, antiviral active substances, anti-inflammatory active substances, antipruritic active substances, anaesthetising active substances, for example benzocaine, corticoids, acne agents, antiparasitic active substances; externally applicable hormones; venous therapeutics; immunosuppressants etc., all for dermal or transdermal use.

Preferred therapeutic agents for dermal and transdermal use are agents for treating skin diseases such as neurodermatitis, atopic dermatitis etc., and antiherpes agents, and also, in particular, those which are employed in the field of wound treatment, in particular for treating chronic wounds, decubitus ulcer, varicose ulcer, diabetic foot syndrome etc., such as, for example, analgesics, for example immunosuppressants, hormones, anaesthetising active substances, antiparasitic, fungicidal or antimycotic and antibacterial active substances such as, in particular, silver-containing active substances such as, for example, silver nitrate, silver chloride, silver iodide or further silver-containing wound-treatment substances known from the state of the art, active substances for supporting and regulating the wound milieu, such as, in particular, electrolytes, silica, mineral substances and trace elements such as, for example, potassium, magnesium, calcium, selenium, iodine etc., active substances for achieving a debridement of the wound, such as, for example, collagenases or other suitable proteolytic enzymes and also active substances for assisting wound healing that are known in the state of the art, such as, for example, growth factors, enzyme inhibitors etc.

Further preferred active substances are those which exhibit a styptic or haemostatic action, such as, for example, thrombin, fibrinogen or cholesteryl sulfate (e.g. sodium cholesteryl sulfate) or active substances with activating action on factors and substances of the extrinsic and/or intrinsic coagulation cascade, such as, for example, phospholipids, kaolin, aprotinin, factor or factor concentrates, tissue factor or calcium ions.

Moreover, it is conceivable to administer further active substances such as bronchial therapeutics such as anti-asthmatics, antitussives, mucolytics etc., antidiabetics such as, for example, glibenclamide, hormones, steroid hormones such as dexamethasone, cardiac glycosides such as digitoxin, cardiac and circulatory therapeutics such as, for example, beta-blockers, anti-arrhythmics, antihypertonics, calcium antagonists etc., psychiatric drugs and antidepressants such as, for example, tricyclic antidepressants (NSMRI), serotonin reuptake inhibitors (SSRI), noradrenalin reuptake inhibitors (NRI), serotonin-noradrenalin reuptake inhibitors (SNRI), monoamine-oxidase inhibitors (MAO inhibitors) etc., neuroleptics, anticonvulsants or anti-epileptics, hypnotics, sedatives, anaesthetics, gastric therapeutics, intestinal therapeutics, lipid-lowering substances, analgesics such as, for example, antimigraine agents, paracetamol, salicylic acid and salicylic-acid derivatives such as acetylsalicylic acid, diclophenac, ibuprofen, ketoprofen, naproxene etc., antiphlogistics, vasodilatators, diuretics, gout remedies, cytostatics, muscle relaxants, contraceptives, for example in the form of hormone plasters, addiction-weaning agents in the form of, for example, nicotine plasters, plant extracts, provitamins such as, for example, beta-carotin, vitamins such as, for example, vitamin C, A, B, E etc., via a transdermal application in a composition according to the invention, for example in the form of a transdermal active-substance patch.

The carrier materials, in particular those on the basis of proteinogenic polymers such as, in particular, collagen or plant polymers such as polysaccharides, may also have certain therapeutic effects. Accordingly, the collagen which is preferably used acts haemostatically and displays a positive, assisting effect in wound healing. The hydrocolloid (sodium) alginate which is preferably used is also said to have a certain haemostatic action. Furthermore, to a certain extent it acts antivirally. Hyaluronic acid is said to have a certain action in re-epithelialisation and as antioxidant and moisture-donor in skin care. They are, however, not active substances in the sense of the invention.

The stratiform biomatrix according to the invention may further include at least one auxiliary substance.

Auxiliary substances include: pH-setting agents, such as buffer substances, inorganic and organic acids or bases; fatty substances, such as mineral oils, such as paraffin oils or vaseline oils, silicone oils, plant oils such as coconut oil, sweet-almond oil, apricot oil, maize oil, jojoba oil, olive oil, avocado oil, sesame oil, palm oil, eucalyptus oil, rosemary oil, lavender oil, pine oil, thyme oil, mint oil, cardamom oil, orange-blossom oil, soya oil, bran oil, rice oil, rapeseed oil and castor oil, wheat-germ oil and vitamin E isolated therefrom, evening-primrose oil, plant lecithins (e.g. soya lecithin), sphingolipids/ceramides isolated from plants, animal oils or fats, such as tallow, lanolin, butter oil, neutral oil, squalane, fatty acid esters, esters of fatty alcohols, such as triglycerides, and waxes with a melting-point corresponding to the temperature of the skin (animal waxes such as bees wax, carnauba wax and candelilla wax, mineral waxes such as microcrystalline waxes, and synthetic waxes such as polyethylene waxes or silicone waxes), and also all the oils suitable for cosmetic purposes (so-called cosmetic oils), as mentioned, for example, in the CTFA treatise entitled Cosmetic Ingredient Handbook, 1. Edn., 1988, The Cosmetic, Toiletry and Fragrance Association, Inc., Washington, surface-active agents in addition to the aforementioned wax surfactants, such as dispersing agents, wetting agents, emulsifiers etc.; fillers; stabilisers; cosolvents; pharmaceutically and cosmetically customary or other dyestuffs and pigments, in particular those which are primarily employed for the purpose of colouring the hydrogel composition and not for the purpose of application and colouring on the human body, such as those pigments and dyestuffs such as the decorative dyestuffs listed under the group of active substances; preservatives; plasticisers; lubricants or release agents; etc.

Auxiliary substances that are preferred in accordance with the invention are fats and oils. In this connection, in particular cosmetic oils as listed above, in particular triglycerides, particularly preferably caprylic/hexanoic acid triglycerides, squalane or jojoba oil, are preferred.

Generally the classification of the aforementioned substances in the category of the auxiliary substances within the scope of the present invention does not exclude the possibility that these auxiliary substances may also display certain cosmetic and/or therapeutic actions, which applies, to a particular degree, to the stated cosmetic oils which are preferably employed.

The stratiform biomatrix according to the invention is obtainable by a process comprising the following steps:
a) producing an aqueous suspension or a solution of at least one structure-forming polymer;
b) optionally, mixing in one or more active substances and/or auxiliary substances;
c) pouring the mixture into a suitable mould;
d) drying the mixture;
e) cutting the dried moulding obtainable from step d) into layers, preferentially of at most 8 mm thickness; optionally
f) cutting the layers from step e) into the desired geometrical configuration of the stratiform biomatrix (1);
g) putting the continuous, straight-through perforations (3) into place and as a result forming regularly shaped, evenly arranged portions (2); and also optionally
h) sterilising and/or fabricating.

In one embodiment, including carrier materials from the group of the aforementioned bioabsorbable synthetic or modified natural polymers, in step c) the aqueous suspension or solution of at least one structure-forming polymer according to step a) is poured into such a bioabsorbable polymer exhibiting a skeletal structure, preferentially into a polylactide skeleton or of a copolymer thereof. Hence the term 'mould' from step c) also encompasses, by definition, a mould constituted by such a bioabsorbable polymer with skeletal structure.

As a rule, however, by the term 'mould' a conventional volume mould or hollow mould in the conventional sense is to be understood.

In the process according to the invention the perforation in step g) can be generated by means of cutting or punching. In this connection it is, in particular, also possible to implement the perforations by means of an appropriately suitable number of perforating tools arranged in parallel with the desired spacing, preferentially knives or conventional roller-type punches.

In a preferred embodiment the perforations are put into place by means of an appropriately suitable number of perforating tools arranged in parallel with the desired spacing, in the form of continuous, preferentially linear, straight-through perforations (3a) arranged parallel to one another, and in the form of continuous, preferentially linear, straight-through perforations (3b) arranged parallel to one another and intersecting the perforations (3a). In this connection the spacing of the perforating tools arranged in parallel may in each instance be the same or different. In this connection, the continuous, straight-through perforations (3a) arranged parallel to one another and the continuous, straight-through perforations (3b) arranged parallel to one another and intersecting the perforations (3a) are preferentially implemented in each instance in one step.

The perforations (3) are preferably formed in such a way that portions (2) connected by perforations are formed having a size of at most 5 cm$^2$.

Furthermore, it is preferred to implement the drying in step d) by means of freeze drying, so a particularly preferred embodiment relates to freeze-dried stratiform biomatrices (1).

Moreover, it is possible to tailor the stratiform biomatrices obtainable in step e) or f) prior to the placing of the perforations in the desired geometrical shape or configuration and optionally to provide them with a colour imprint. It is, for example, conceivable, by imprinting of the stratiform biomatrix, to apply a type of cutting pattern or separating pattern in the form of a coloured marking which predetermines a suitable contour for an undoing of the perforations for the purpose of severing suitable subsegments.

In particular, in the therapeutic use the sterilisation of the stratiform biomatrices according to the invention is of significance. This sterilisation can be carried out by known and customary methods.

For the use according to the invention of the stratiform biomatrix, on the one hand good wetting properties or adsorption properties of the carrier materials being used are of significance, for the aforementioned reasons.

Furthermore, for the aforementioned reasons in particular a high mechanical stability, such as, in particular, a high tear strength, of the carrier materials being used is crucial. The wet tear strength of the carrier materials that are preferred in accordance with the invention, determined in accordance with DIN EN ISO 3376 prior to the placing of the perforations according to the invention onto the stratiform carrier materials, preferably amounts to at least 50 mN/mm layer thickness, more preferably 100 mN/mm, still more preferably 200 mN/mm.

With the use of a method for determining the tear strength by means of a punch (internal measuring method UV 8801), on biomatrices perforated in accordance with the invention and on non-perforated biomatrices a metal punch with a spherical head (25 mm in diameter) is pressed onto the fleece with the aid of a mechanical testing instrument (Zwick materials testing instrument B Z 2.5/TN 1S), and the distance and the force that the punch travels and exerts, respectively, are recorded.

For the experiment the stratiform biomatrix is tailored to a size of 8 cm×8 cm and is introduced into the sample receptacle of the instrument. Subsequently the measurement is started and the spherical punch presses onto the sample until a tearing of the material occurs. For the determination of the wet tear strength the sample is completely moistened prior to the start of the measurement. In the case of the determination of the dry tear strength the sample is not moistened but is gauged dry.

The force at which a tear of the material occurs is recorded by means of electronic data recording, is calculated and output. Preferred wet tear strengths of the carrier materials that are preferred in accordance with the invention prior to the placing of the perforations according to the invention, determined by this internal method (UV 8801), amount to >20 cN/mm layer thickness, more preferably >30 cN/mm, still more preferably >40 cN/mm.

By virtue of the perforations that have been put into place in accordance with the invention, the tear strength is, as expected, distinctly diminished, as a result of which the possibility, described above, of the simple severing of subsegments is made possible. For instance, an unperforated freeze-dried stratiform biomatrix consisting of collagen has a dry tear strength, measured by the above method UV 8801, that is about four times as high as a corresponding collagen biomatrix that has been provided with the perforations according to the invention, forming square portions measuring 1 cm×1 cm. In comparison with perforated biomatrices with portions having a size of 0.5 cm×0.5 cm, the dry tear strength, according to the above method UV 8801, is higher by about a factor of 8. In the case of alginate-based freeze-dried biomatrices, by virtue of a perforation according to the invention, forming square portions having a size of 1 cm×1 cm, correspondingly a reduction of the dry tear strength by about a factor of 12 can be observed.

Moreover, in particular also for aesthetic reasons, particularly in the cosmetic use but also in the therapeutic use, such biomatrices are desirable, the carrier material of which is provided with a high optical density. In this connection the term 'optical density' designates the quantitative unit optical density, measured as the common logarithm of the quotient of transmitted light intensity and incident light intensity, ascertained with a Heiland SW densitometer TD 03 in respect of stratiform carrier materials having a layer thickness of 1 mm, measured prior to the placing of the perforations according to the invention onto the stratiform carrier materials. The carrier materials of the present invention preferably have an optical density of ≧0.02, more preferably ≧0.03, still more preferably ≧0.05, per mm of layer thickness.

In this connection a high optical density is, for example, advantageous for such stratiform biomatrices which are to be provided with coloured imprints, for example in the form of aesthetic shapings and colourings, letterings, logos or explanatory notes for use, or the aforementioned markings.

The stratiform biomatrices according to the invention may have been individually packed, this being preferred, in particular, in the therapeutic or pharmaceutical use but also in the professional cosmetic use. Tailored cuts for the cosmetic use may also be present in a plurality, side by side or on top of one another in contact in a suitable receptacle or in a suitable packaging.

The stratiform biomatrices according to the invention serve for external cosmetic use and also for external and transdermal pharmaceutical use. In this connection the external use takes place, as a rule, in such a way that the stratiform biomatrices or the subsegments severed therefrom along the perforations prior to use are applied onto the parts of the body to be treated or are applied dry in the wound and are moistened and rehydrated there with water or with an aqueous solution that contains one or more active substances and/or one or more auxiliary substances (a so-called activator solution). It is, however, also possible to moisten the stratiform biomatrices according to the invention or subsegments thereof prior to application onto the part of the body to be treated, or to make already pre-moistened stratiform biomatrices available in a suitable packaging.

A further subject of the present invention is a care set or treatment set containing at least one of the stratiform biomatrices described previously.

Furthermore, the present invention relates to the use of the stratiform biomatrices (1) for the purpose of cosmetic and/or therapeutic treatment. In particular, a subject of the present invention is to use the stratiform biomatrices described above as agents for treating acute wounds such as, for example, traumatic or surgical wounds, for example tumour wounds, and also for treating chronic wounds such as, for example, decubitus ulcer, varicose ulcer, diabetic foot syndrome etc. In this connection the stratiform biomatrices can be used either as temporary overlay or as implant. Particularly preferred in accordance with the invention in this connection is the use in the treatment of chronic wounds and also the use as haemostyptic. The stratiform biomatrices according to the invention may in this connection constitute pharmaceutical products or medical products.

Moreover, the stratiform biomatrices according to the invention described above may also be used in a vacuum-assisted wound-treatment therapy such as is known from the state of the art and such as is described, for example, in US 2007/0027414. In this connection the stratiform biomatrices according to the invention in such a vacuum treatment can, by reason of the high flexibility described above, be introduced optimally into the wound bed and can, by reason of their good absorption properties and hydration properties, positively assist the removal of the excess wound secretion there. In this connection the transportation of secretion through the permeable biomatrix material is, on the one hand, already obtained through the choice of a hydrophilic matrix material. Furthermore, in particular the freeze-dried biomatrices that are preferred in accordance with the invention are provided with a high porosity by reason of the freeze-drying process, additionally facilitating the passage of liquid. In addition, by virtue of the perforations according to the invention the permeation capacity of the biomatrices is additionally enhanced. The use of freeze-dried porous materials, optionally also of those which have been provided with hole-type perforations, is already known in principle in vacuum therapy. In this connection, however, through the high flexibility and hence spatial modulation capability, achieved by virtue of the special perforation, in combination with the improved permeation effect, achieved by virtue of the perforations, in particular the perforated stratiform biomatrices according to the invention can be employed particularly effectively in a vacuum-assisted wound-treatment therapy. In particular, stratiform biomatrices consisting of carrier materials that in themselves already have a positive influence on the progress of wound healing, such as, for example, the collagen carrier materials that are preferred in accordance with the invention, are in this connection particularly suited and preferred to be used in a vacuum therapy. Here too, in principle a temporary use is possible, during which the stratiform biomatrix is removed from the wound or is partially degraded in the course of the treatment and is flushed out of the wound together with the wound secretion, or the stratiform biomatrix can remain in the wound as implant and is either degraded or metabolised there or is infiltrated by cells and incorporated into the body in the course of the epithelialisation of the wound.

The present invention also relates, moreover, to a combination including at least one of the stratiform biomatrices according to the invention and also at least one aqueous solution that contains one or more active substances and/or at least one or more auxiliary substances (a so-called activator solution) in a spatial arrangement belonging together (application package, set, kit of parts etc.). In this connection, in the case of the active-substance solution it may be a question, for example, of solutions of readily volatile active substances and/or auxiliary substances which by reason of the production process, for example by virtue of the freeze drying, are not to be introduced or cannot be introduced into a freeze-dried biomatrix, such as, for example, certain portions of essential oils, perfumes etc. Such active substances and/or auxiliary substances may also be contained that achieve a moistening action which, particularly in the case of external use on the skin, is desired and preferred, and that, by reason of this moistening action or by reason of hygroscopic tendencies, cannot be worked into the freeze-dried biomatrices that are preferred in accordance with the invention, or can only be worked into them in small amounts, since as a result the stability of moisture-deficient active substances which are possibly contained can no longer be maintained. As a matter of principle, one or more of the aforementioned active substances and/or auxiliary substances may be contained in the activator solutions.

In particular, such active-substance solutions may also be contained in the kit-of-parts configurations that are suitable for therapeutic use, such as, for example, for the purpose of rehydrating and cooling burns, in particular in the course of the acute dressing and initial dressing of burn injuries or for use in a moist wound dressing. As a matter of principle, such rehydrating or wound-treatment solutions are known from the state of the art. In this connection it is a question, as a rule, of physiological solutions or electrolyte-containing solutions which may optionally contain further suitable active substances, as stated above. In the embodiments that are preferred in accordance with the invention it is a question, as a rule, of aqueous activator solutions or rehydration solutions, for which reason the combination in a kit-of-parts arrangement with a stratiform biomatrix according to the invention, consisting of a hydrophilic, open-pore, absorbent carrier material, is then particularly preferred. An open-pore spongy foam structure, such as is present, in particular, in the case of freeze-dried carrier materials, is particularly preferred, since as a result the carrier material of the stratiform biomatrix has a high absorbency and also, given selection of suitable polymers, for example from the group comprising collagen, alginates and hyaluronic acid, ideally also has a high liquid-uptake and liquid-retaining capacity. This is of particular significance particularly with the use of such embodiments for the initial dressing of fire-injured persons or in moist wound treatment, since in these cases it is particularly important to supply a large amount of the active-substance solution to the wound and to keep it there. This is made possible by virtue of the fact that the liquid penetrates into the pores of the preferred open-pore, absorbent polymer carrier and is retained therein.

Another important effect of such preferred uses lies in the possibility of simple and large-area dissipation of heat, by a cooling action being generated via the evaporation of the liquid. A cooling is not only advantageous in connection with the treatment of burn injuries or wounds that exhibit an increased evolution of heat by reason of an inflammatory reaction, but also in the case of damaged skin, for example as a consequence of cases of sunburn or sports injuries, and also generally for the purpose of alleviating painful and unpleasant inflammations of the skin, and also for the purpose of alleviating side-effects of irritant cosmetic treatments, such as, for example, peeling treatments, laser treatments, Fraxel treatments or resurfacing treatments. In this connection it is, in particular, desirable to cause the cooling effect to persist over a longer period, which, in particular, can be obtained by means of the particularly preferred hydrophilic, open-pore, absorbent carrier materials described above.

A hydrophobic carrier material would be unable to absorb an aqueous active-substance solution. The use of a hydrophobic carrier material in combination with a hydrophobic active-substance solution, for example on the basis of fats and oils, is disadvantageous and therefore undesirable by reason of the closure of the wound (so-called occlusion), with prevention of transmission and heat dissipation.

The configuration of such kit-of-parts combinations of stratiform biomatrix according to the invention, on the one hand, and active-substance solution, on the other hand, may provide that the two constituents are taken out of the kit-of-parts arrangement separately and are brought together outside it for further use. It is, however, also conceivable that a bringing-together of the components even takes place within the kit-of-parts packaging, for example in chambers provided for them, and the hydrated composition is then supplied directly from said packaging for further cosmetic or pharmaceutical external or transdermal use. This may, for example, also be carried out directly by the end user.

The invention claimed is:

1. A stratiform biomatrix that is formed from regularly shaped uniformly arranged portions which are separably connected to one another by continuous, straight-through perforation configurations, which form weakening-lines between the regularly shaped uniformly arranged portions.

2. A stratiform biomatrix according to claim 1, wherein the regularly shaped uniformly arranged portions are substantially triangular, rectangular, honeycombed, circular or elliptical.

3. The stratiform biomatrix according to claim 1, wherein the regularly shaped uniformly arranged portions are formed from continuous linear, straight-through perforation configurations arranged parallel to one another and from continuous linear, straight-through perforation configurations arranged parallel to one another and intersecting the perforations and wherein the spacings between the perforation configurations arranged in parallel and/or between the perforations arranged in parallel and intersecting each other are in each instance the same or different.

4. The stratiform biomatrix according to claim 1, wherein the regularly shaped uniformly arranged portions have a size of at most 5 cm$^2$ and wherein the size of the portions is in each instance the same or different.

5. The stratiform biomatrix according to claim 1, wherein the biomatrix is formed of a carrier material including at least one structure-forming hydrophilic polymer selected from the group consisting of natural polymers, animal hydrocolloids, and plant hydrocolloids, and also, and optionally one or more active substances and/or auxiliary substances.

6. The stratiform biomatrix according to claim 5, wherein the structure-forming polymer is selected from the group consisting of collagens, polysaccharides, alginates, and combinations thereof.

7. The stratiform biomatrix according to claim 5, wherein the active substance is selected from the group consisting of haemostatic agents, wound-treatment agents, and combinations thereof.

8. The stratiform biomatrix according to claim 6, wherein the active substance is selected from the group consisting of haemostatic agents, wound-treatment agents, and combinations thereof.

9. The stratiform biomatrix according to claim 1, wherein the biomatrix is freeze-dried.

10. A process for producing a stratiform biomatrix according to claim 1, comprising the following steps:
   a) producing an aqueous suspension or a solution of at least one structure-forming polymer;
   b) optionally, mixing in one or more active substances and/or auxiliary substances;
   c) pouring the mixture into a suitable mould;
   d) drying the mixture;
   e) cutting the dried moulding obtainable from step d) into layers of at most 8 mm thickness; optionally
   f) cutting the layers from step e) into the desired geometrical configuration of the stratiform biomatrix;
   g) putting the continuous, straight-through perforation configurations into place and thereby forming regularly shaped, uniformly arranged portions which are separably connected to one another by the continuous, straight-through perforation configuratios which are in the form of weakening-lines between the regularly shaped uniformly arranged portions and also optionally
   h) sterilising and/or fabricating.

11. The process according to claim 10, wherein in step g) perforations in the form of continuous linear, straight-through perforation configurations arranged parallel to one another and in the form of continuous linear, straight-through perforation configurations arranged parallel to one another and intersecting each other are put into place in each instance in one step by means of an appropriately suitable number of perforating tools arranged in parallel with the desired spacing, the spacing between the perforating tools arranged in parallel being the same or different.

12. The process according to claim 10, wherein in step g) the perforations are formed in such a way that portions connected by the perforation configurations are formed having a size of at most 5 cm$^2$.

13. The process according to claim 11, wherein in step g) the perforations are formed in such a way that portions connected by the perforation configurations are formed having a size of at most 5 cm$^2$.

14. A cosmetic and/or therapeutic method of treating the skin comprising applying to skin the stratiform biomatrix according to claim 1.

15. A cosmetic and/or therapeutic method of treating the skin comprising applying to skin the stratiform biomatrix according to claim 2.

16. A method of treating wounds comprising applying the stratiform biomatrix according to claim 1 to at least one of bleeding wounds, hemorrages, acute wounds, and chronic wounds or by implanting said stratiform biomatrix into a body part, thereby promoting hemostasis and/or wound healing.

17. A method of treating wounds comprising applying the stratiform biomatrix according to claim 2 to at least one of bleeding wounds, hemorrages, acute wounds, and chronic wounds or by implanting said stratiform biomatrix into a body part, thereby promoting hemostasis and/or wound healing.

18. The method of claim 16 wherein the stratiform biomatrix is part of a in a vacuum-assisted wound-treatment device.

19. A kit-of-parts combination containing at least one stratiform biomatrix according to claim 1 and also at least one aqueous solution that contains one or more active substances and/or one or more auxiliary substances.

20. The process of claim 10, wherein drying in step d) is freeze drying.

* * * * *